United States Patent [19]
Duff

[11] Patent Number: 5,338,454
[45] Date of Patent: Aug. 16, 1994

[54] CHIRAL MOBILE PHASE ADDITIVES FOR IMPROVED LIQUID-CHROMATOGRAPHY SEPARATIONS

[75] Inventor: Keith J. Duff, Howard, Pa.

[73] Assignee: Supelco, Incorporated, Bellefonte, Pa.

[21] Appl. No.: 936,158

[22] Filed: Aug. 27, 1992

[51] Int. Cl.⁵ ............................................. B01D 15/08
[52] U.S. Cl. .................... 210/635; 210/656; 210/198.2; 95/82; 95/88; 96/101
[58] Field of Search .............. 210/635, 656, 198.2, 210/502.1; 95/82, 88; 96/101; 436/161

[56] References Cited

U.S. PATENT DOCUMENTS 4,290,893 9/1981 Hare ................................. 210/198.2

OTHER PUBLICATIONS

M. Fujita, et al., "Highly Efficient Chromatographic Resolution of Co(en)3 3+Ion with a Column of TA(ES) Sephadex Containing D-Tartrate Groups", Chem. Lett., Chem. Soc. Japan (1975) pp. 473–474.
C. Pettersson and C. Gioeli, J. Chrom. 435 (1988) pp. 225–228, "Improved Resolution of Enantiomers of Naproxen By The Simultaneous Use of a Chiral Stationary Phase and a Chiral Additive in the Mobile Phase".

Primary Examiner—Ernest G. Therkorn
Attorney, Agent, or Firm—Senniger, Powers, Leavitt & Roedel

[57] ABSTRACT

Chromatographic separations and resolutions of racemic mixtures and diastereoisomers are enhanced by simultaneously employing an enantiomeric, chiral stationary phase (CSP) and an enantiomeric, chiral mobile phase additive (CMPA) bearing a stereoisomeric relationship to the CSP but having the opposite chirality are enhanced relative to the use of either a CSP or a CMPA alone. Specific CMPA compositions having the structural formulas

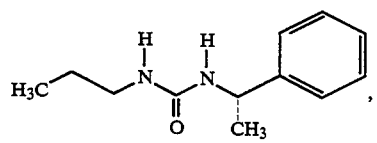

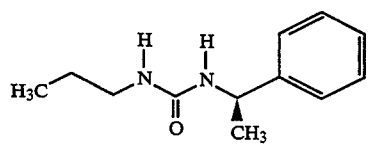

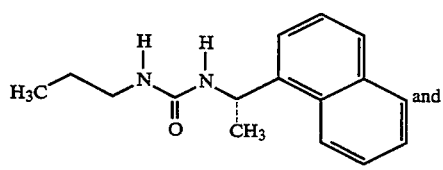

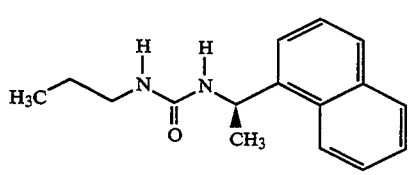

are also disclosed.

16 Claims, No Drawings

CHIRAL MOBILE PHASE ADDITIVES FOR IMPROVED LIQUID-CHROMATOGRAPHY SEPARATIONS

FIELD OF THE INVENTION

This invention relates to a liquid-chromatographic separation method, and more particularly to a method of separating enantiomers and diastereoisomers wherein a chiral stationary phase (CSP) is used with a chiral mobile-phase additive (CMPA) having a stereoisomeric relation to the CSP.

BACKGROUND OF THE INVENTION

The separation of enantiomers and diastereoisomers (chiral separations) is a growing concern to modern chemists. Enantiomers of racemic drugs and agricultural chemicals, for example, frequently exhibit different degrees of activity and toxicity in biological systems, even though they differ from one another by only a rotational configuration of the molecule. Isolation of the individual enantiomers allows the specific properties of each to be determined.

Chiral separations are one of the most challenging types of purifications because of the extreme similarity between the two components in the racemic mixture; each is merely a mirror image of the other. Others have used chiral liquid chromatographic separations employing either a CSP or a CMPA as the chiral discriminating agent.

Using both a CSP and a CMPA is less frequent, but a publication by M. Fujita, et. al., "Highly Efficient Chromatographic Resolution of [Co(en)$_3$]$^{3+}$ Ion with a Column of TA(ES)Sephadex Containing D-Tartrate Groups", Chem. Lett., Chem. Soc. Japan (1975) pp. 473–474, described an improvement in the separation of Cobalt(III) complexes by using sodium L-tartrate as a CMPA in columns packed with partially esterified D-tartrate-Sephadex. One would expect these columns to be relatively unstable because of the likelihood that the ester functionality would hydrolyze and transesterify. In a related study, Pettersson and Gioeli, J. Chrom. 435 (1988) 225, used quinine as a CMPA to improve separation on an alkylquinidine-silica CSP. Quinine is not an actual enantiomer or diastereomer of the alkylquinidine, but appears to behave similarly. The poor predictability of analyte elution order with different mobile-phase additives may have resulted from this lack of true enantiomeric relationship between the additive and the CSP.

SUMMARY OF THE INVENTION

I have discovered a liquid-chromatographic method suitable for the separation of enantiomers and diastereoisomers which comprises passing a liquid mobile phase containing dissolved analytes, which analytes may include enantiomers, diastereoisomers, or mixtures thereof, through a chromatographic column containing an enantiomeric, chiral stationary phase (CSP) covalently bonded through a stable bond to a support, wherein the mobile phase further contains an enantiomeric, chiral mobile-phase additive (CMPA) which bears a stereoisomeric relation to the CSP. The CMPA is selected such that the asymmetric carbon atom or atoms of the CSP and the groups attached thereto, excluding the linking group, are repeated in the chiral mobile-phase additive, but with opposite chirality. The linking group on the chiral stationary phase is structurally homologous to the linking group on the chiral mobile-phase additive. This method shows increased selectivity and resolution of mixed enantiomers or diastereoisomers, e.g., racemic mixtures, compared to methods in which no CMPA is used, the CMPA does not repeat the groups attached to the assymetric carbon atom or atoms of the CSP, or the CMPA and CSP have the same, rather than opposite, chirality.

I have further discovered specific chemical compounds useful as CMPA's in the method of the present invention, those chemical compounds having the structures

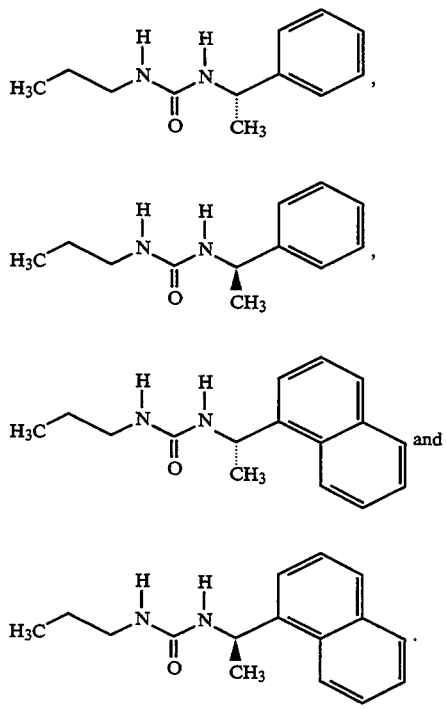

DETAILED DESCRIPTION OF THE INVENTION

According to the present invention, the structures of the CSP and the CMPA bear a stereoisomeric relationship to one another, but with opposite chiralities. As used herein, that is intended to mean that both the CSP and the CMPA contain one or more asymmetric carbon atoms, each having four different groups attached to it, where the four groups are the same for the CMPA and the CSP, except that one of the four groups of the CSP is also attached covalently to the support for the CSP. That group on the CSP which is attached to the support is termed herein the "linking group", and the corresponding group on the CMPA is also termed the "linking group", even though the covalent bond to the support is absent from the linking group on the CMPA. The linking group on the CMPA need not contain exactly the same number of carbon atoms as the CSP linking group, but it must be structurally homologous that linking group, and preferably contains one carbon atom more or less than the linking group on the CSP. Preferred for the linking group is an alkyl group. When the CMPA bears this relationship to the CSP, its presence in the mobile phase enhances the separation of enantiomers and diastereoisomers.

In contrast, when the chiralities of the CSP and the CMPA are the same, the enhancement is not seen, and indeed a degradation of the separation may be seen. Accordingly, use of a CMPA bearing a stereoisomeric relationship to the CSP, where both the CSP and the CMPA have the same chirality, is not contemplated as being within the scope of the present invention. Thus, enhancement of separation occurs when the (S)-CMPA is used in conjunction with the (R)-CSP (e.g., Formula I(a), below, with Formula I(b)), and when the (R)-CMPA is used with the (S)-CSP (e.g., Formula II(a), below, with Formula II(b)). Reduced or no enhancement occurs when the (S)-CMPA is used with the (S)-CSP, and when the (R)-CMPA is used with the (R)-CSP.

The term, enantiomeric, as used herein, indicates that the chiral substance to which it is applied is the optically active form, that is, it is not a racemic mixture of the two enantiomers. Similarly, two substances which are enantiomers of one another, or bear an enantiomeric relationship to one another, have opposite chiralities.

Preferred structures for the CSP and its enantiomeric CMPA are

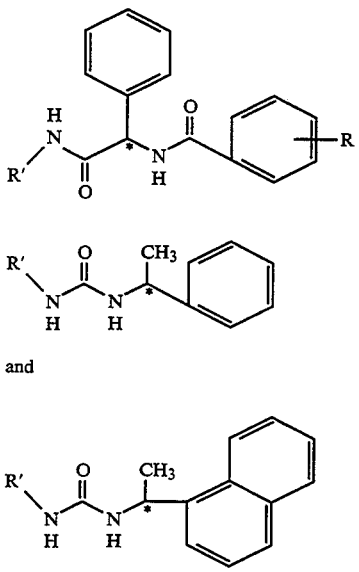

wherein
R is one or more electron-withdrawing groups, and
R' is a $C_1$–$C_{20}$ aryl or linear or branched alkyl group
In the above structures, the asterisk indicates the chiral carbon atom.

The electron-withdrawing group or groups, R, may be, for example, trifluoromethyl (—$CF_3$), nitro (—$NO_2$) or halo. Preferably R is nitro, and more preferably 4-nitro, 3,5-dinitro or 2,4-dinitro. Where R is halo, preferred is the group consisting of chloro, fluoro and bromo, and still more preferred is chloro, as for example mono-, di- and trichloro. R' may be a $C_1$–$C_{20}$, linear or branched alkyl. R' may include, for example, methyl; ethyl; propyl; propyl substituted with a methyl group; butyl, butyl substituted with one or more methyl or ethyl groups; hexyl; octyl; decyl; dodecyl; tetradecyl; hexadecyl; octadecyl; and eicosyl; each of these alkyl groups may be substituted with one or more $C_1$–$C_4$ alkyl groups, the total number of carbons being 20 or fewer. Preferred for R' is $C_2$–$C_8$ alkyl, and more preferred is propyl.

The method of the present invention involves passing the mobile phase through a column containing an enantiomeric CSP. The mobile phase is a liquid containing dissolved components to be separated; preferably it is a liquid solvent for the components to be separated and the CMPA, and is inert to them and to the CSP as well. Still more preferably the liquid mobile phase is low in flammability, toxicity and levels of other safety and environmental hazards, and has a sufficiently low viscosity at the temperature and pressure employed to provide acceptable flow rates through the column, as for example at least about 0.1 ml/minute. Such a mobile phase may be readily selected by one skilled in the art. Examples of mobile phases useful in the present invention include hydrocarbons such as hexane, cyclohexane, heptane, benzene and the like, alcohols such as methanol, ethanol, n-propanol, isopropanol and the like, esters such as ethyl acetate, ethyl propionate, butyl acetate and the like, ketones such as acetone, methyl ethyl ketone and the like, nitriles such as acetonitrile, propionitrile and the like, and water.

The enantiomeric CSP is supported in the column by a particulate support, and is preferably covalently bonded to the support. The support may be selected from a wide range of materials that are insoluble in the mobile phase, are solid at the temperature used for the HPLC separation, and contain or can be modified with an enantiomeric CSP. The support is preferably porous, but non-porous supports, e.g. glass beads, may also be used, at the expense of sample capacity. Inorganic supports including silica, alumina, glass and the like, and organic supports including cellulose, modified celluloses, chitin, cyclodextrin, crosslinked styrenic polymers, partially carbonized styrenic polymers, phenolic polymers and the like are supports useful in the present invention. Silica is a preferred support. The CSP is bonded to the support through a covalent bond having relatively high stability, as for example to hydrolysis or thermal degradation. Covalent bonds useful to bond the CSP of the present invention to the support include methylene, carbon-silicon, urea, amide, ether, ketone and thioether bonds. The preferred level of CSP on the support is from about 1 to about 10 micromoles per square meter of support surface area ($\mu m/m^2$), and more preferably from about 3 to about 5 $\mu m/m^2$.

The chromatographic conditions for the separation are not critical to the present invention, and may be selected readily by those skilled in the art. The temperature selected should be above the freezing point and below the boiling point of the mobile phase at the pressure employed, and low enough to prevent excessive decomposition of the dissolved analytes, the CSP or the CMPA. A preferred temperature range is from about $-10°$ to about $120°$ C., more preferably from about $0°$ to about $100°$ C., and still more preferably from about $10°$ to about $80°$ C. The pressure differential across the chromatographic column is selected to provide an adequate flow of mobile phase through the column and to remain within the pressure limits of the column, pump and other components of the HPLC system. A preferred pressure range is from about 20 kiloPascals to about 20 megaPascals and more preferably from about 150 kiloPascals to about 10 megaPascals. Flow rates through the column are selected to be as rapid as practical within the constraints of the above parameters and adequate separation of analytes; a preferred range of flow rates is from about 0.1 ml/minute to about 100 ml/minute, more preferably from about 1 ml/minute to about 50 ml/minute.

The CMPA of the present invention is present in the mobile phase at a concentration of from about 0.001 millimoles per liter (mM) to saturation of the CMPA in the mobile phase, preferably from about 0.1 mM to about 1 mM, and more preferably from about 0.2 mM to about 0.3 mM.

Equipment for high-performance liquid chromatography (HPLC) is well known to those skilled in the art, and is suitable for use in the method of the present invention. Such equipment typically includes pumping means, means to inject into the mobile phase a sample containing components to be separated, the column containing the CSP, and appropriate conduits and connections for assembling this equipment such that the mobile phase flows continuously from the injection means into and through the column.

are washed with a non-polar organic solvent; no further purification is necessary prior to their use as CMPA materials in the process of the present invention.

An example of an (R)-CSP is illustrated in Formula I(a). The preferred CMPA stereoisomeric to that CSP but having opposite chirality, i.e., the (S)-CMPA of the present invention, is shown in Formula I(b). Similarly, Formula II(a) illustrates the (S)-CSP stereoisomeric to that of Formula I(a), and Formula II(b) shows the preferred CMPA stereoisomeric to it but having opposite chirality, i.e., the (R)-CMPA. As explained above, the (S)-CMPA does not improve separations on the (S)-CSP and the (R)-CMPA does not improve separations on the (R)-CSP.

FORMULA I

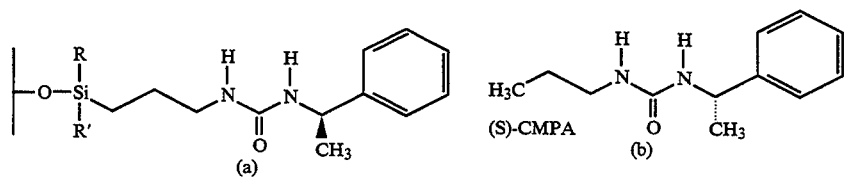

FORMULA II

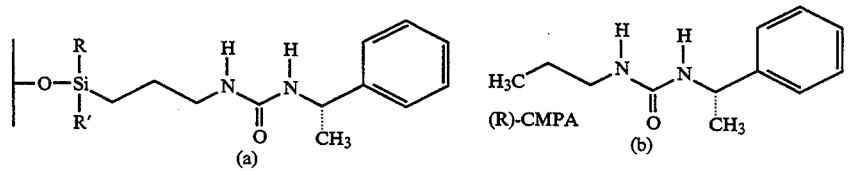

Other examples of preferred CSP's, and the corresponding CMPA's of the present invention having a stereoisomeric relationship but opposite chirality to them, are shown in Formulas III and IV.

FORMULA III

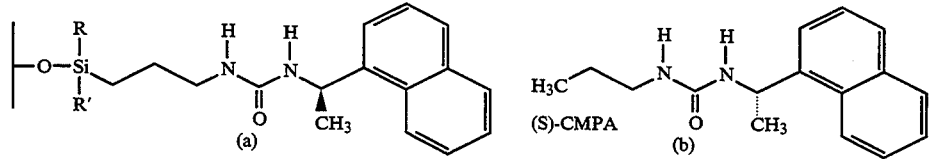

FORMULA IV

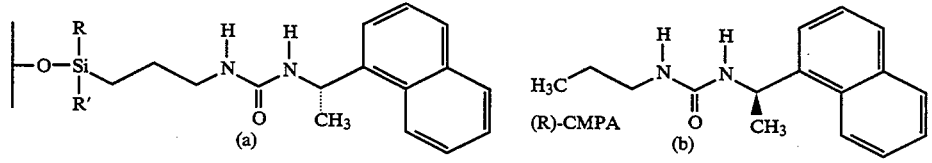

Subsequent to its passage through the column containing the CSP, the mobile phase is preferably conducted to a detector where components of the mobile phase may be detected as they elute from the column. The detector may be any detector known to those skilled in the art having an appropriate sensitivity to the separated components, as for example ultraviolet transmission, circular dichroism, refractive index, electrochemical or mass spectrometer detectors.

The CMPA compounds of Formulas I(b), II(b), III(b) and IV(b), below, are novel. They are easily prepared from the corresponding amine by reacting it with n-propyl isocyanate under conditions which will be readily apparent to those skilled in the art. Once prepared, the CMPA compounds of the present invention In each of the above formulas, R and R' are selected independently from $C_1$-$C_8$ alkyl, methoxy, ethoxy, aryl and the like.

The following examples are intended to illustrate the invention and not to limit it except as it is limited in the claims. All ratios and percentages herein are by weight unless otherwise specified, and all reagents are of good commercial quality unless otherwise specified.

EXAMPLE 1

This example illustrates preparation of the chiral mobile-phase additive of Formula I(b).

A solution of 9.40 g (S)-(−)-α-methylbenzylamine in 200 ml of HPLC-reagent-grade hexane was stirred under nitrogen, and 17.3 g n-propylisocyanate was added dropwise; stirring was continued overnight. The white precipitate of Formula I(b) was collected by vacuum filtration, washed three times with hexane and vacuum dried; the yield of dried precipitate was 15.9 g, or 99% of theoretical, and the precipitate had a melting range of 99.5°–101.0° C. Theoretical elemental content for $C_{12}H_{18}N_2O$, and elemental analysis values for the precipitate are shown in Table I, below.

EXAMPLE 2

This example illustrates preparation of the chiral mobile-phase additive of Formula II(b). The procedure of Example 1 was repeated using (R)-(+)-α-methylbenzylamine, and the yield was 16.0 g, or 100% of theoretical, of white precipitate having a melting range of 98.0°–99.5° C. Theoretical elemental content for $C_{12}H_{18}N_2O$ and elemental analysis values for the precipitate are shown in Table I, below.

TABLE I

Elemental Content of CMPA, Formulas I(b) and II(b), $C_{12}H_{18}N_2O$:

| Element | Theoretical Result | Formula I(b) Analytical Value | Formula II(b) Analytical Value |
|---|---|---|---|
| C | 69.87% | 69.92% | 69.86% |
| H | 8.79% | 8.82% | 8.76% |
| N | 13.58% | 13.53% | 13.60% |

EXAMPLE 3

This example illustrates preparation of the chiral mobile-phase additive of Formula III(b).

A solution of 0.9415 g (S)-(−)-1-(1-naphthyl)ethylamine in 35 ml of HPLC-reagent-grade hexane was stirred under nitrogen, and 0.515 g n-propylisocyanate was added; stirring was continued overnight. The white precipitate of Formula III(b) was collected by vacuum filtration, washed three times with hexane and vacuum dried; the yield of dried precipitate was 1.362 g, or 97% of theoretical, and the precipitate had a melting range of 170.5°–171.5° C. Theoretical elemental content for $C_{16}H_{20}N_2O$, and elemental analysis values for the precipitate are shown in Table II, below.

EXAMPLE 4

This example illustrates preparation of the chiral mobile phase additive of Formula IV(b). The procedure of Example 3 was repeated, except that 1.00 g of (R)-(+)-1-(1-naphthyl)ethylamine and 0.547 g n-propylisocyanate were used. The yield was 1.47 g, or 98% of theoretical, and the melting range was 169.5°–170.5° C. Theoretical elemental content for $C_{16}H_{20}N_2O$, and elemental analysis values for the precipitate are shown in Table II, below.

TABLE II

Elemental Content of CMPA, Formulas III(b) and IV(b), $C_{16}H_{20}N_2O$:

| Element | Theoretical Result | Formula III(b) Analytical Value | Formula IV(b) Analytical Value |
|---|---|---|---|
| C | 74.97% | 74.74% | 74.96% |
| H | 7.86% | 7.91% | 7.88% |
| N | 10.93% | 11.02% | 10.99% |

EXAMPLE 5

This example illustrates separation of (±)-N-(1-phenethyl)-3,5-dinitrobenzamide and benzene (as a marker) on columns containing the CSP's of Formulas I(a) and II(a), using the CMPA's of Formula I(b) and II(b).

The HPLC equipment was a Waters Automated Gradient Controller, a Waters 712 Wisp injector, a Waters 484 Tunable Absorbance Detector, a Waters 745 Data Module and a Waters 510 HPLC pump. The 25-cm-long×4.6-mm-ID chiral stationary-phase HPLC columns were obtained from Supelco, Inc., and the HPLC conditions were as follows:

| Flow | 1 ml/minute |
|---|---|
| Injection Volume | 10 μl of standard (±)-N-(1-phenethyl)-3,5-dinitrobenzamide solution |
| Detection | Ultraviolet at 254 nm |
| Mobile Phase | 80:20 hexane:ethyl acetate |

Separate injections of (±)-N-(1-phenethyl)-3,5-dinitrobenzamide solution were used for each of four (R)-phenylurea columns (Formula II(a)) and one (S)-phenylurea column (Formula I(a)) and each of four concentrations (0.00, 0.25, 0.50 and 0.75 millimolar) of the CMPA's of Formulas I(b) and II(b) in the mobile phase. The resulting peak-capacity factors were calculated based on the formula:

$$k' = T_r - T_o/T_o$$

where
 $k'$ = peak capacity factor
 $T_r$ = retention time of enantiomer
 $T_o$ = void volume Selectivity and resolution were then calculated as follows:

$$\alpha = k'_2/k'_1$$

where
 α = selectivity
 $k'_1$ = peak capacity factor of the first eluted enantiomer
 $k'_2$ = peak capacity factor of the second eluted enantiomer $$R_s = 2(T_{r2} - T_{r1})/W_1 + W_2$$

where
 $R_s$ = resolution
 $T_{r1}$ = retention time of the first enantiomer peak
 $T_{r2}$ = retention time of the second enantiomer peak
 $W_1$ = width of first enantiomer peak
 $W_2$ = width of second enantiomer peak To establish reproducibility of the results, the entire set of injections was repeated; this repeat is referred to below as the second run. Results of the two sets of injections on the (R)-CSP columns are shown separately below in Tables III and IV, and for the (S)-CSP in Tables V and VI. The selectivity, resolution and peak capacity factors for the enantiomers ($k'_1$ and $k'_2$) shown in the tables are defined by the above equations.

TABLE III

(R)-CSP Results - First Run

| Column | Concentration | Enantiomer | Selectivity | Resolution | $k'_1$ | $k'_2$ |
|---|---|---|---|---|---|---|
| 1 | 0.75 | S | 1.33 | 3.27 | 1.97 | 2.63 |
| 2 | 0.75 | S | 1.34 | 3.54 | 1.94 | 2.59 |
| 3 | 0.75 | S | 1.33 | 3.36 | 1.92 | 2.57 |
| 4 | 0.75 | S | 1.34 | 3.48 | 1.95 | 2.60 |
| 1 | 0.50 | S | 1.33 | 3.73 | 2.05 | 2.72 |
| 2 | 0.50 | S | 1.33 | 3.52 | 2.09 | 2.77 |
| 3 | 0.50 | S | 1.33 | 3.44 | 2.04 | 2.71 |
| 4 | 0.50 | S | 1.33 | 3.55 | 2.14 | 2.84 |
| 1 | 0.25 | S | 1.31 | 3.58 | 2.34 | 3.07 |
| 2 | 0.25 | S | 1.31 | 3.52 | 2.29 | 3.01 |
| 3 | 0.25 | S | 1.30 | 3.56 | 2.64 | 3.42 |
| 4 | 0.25 | S | 1.31 | 3.78 | 2.35 | 3.10 |
| 1 | 0.00 | N | 1.26 | 2.95 | 3.10 | 3.91 |
| 2 | 0.00 | N | 1.26 | 3.04 | 2.91 | 3.68 |
| 3 | 0.00 | N | 1.25 | 2.97 | 3.11 | 3.90 |
| 4 | 0.00 | N | 1.25 | 2.99 | 3.34 | 4.18 |
| 1 | 0.75 | R | 1.22 | 2.42 | 2.06 | 2.49 |
| 2 | 0.75 | R | 1.22 | 2.55 | 1.95 | 2.37 |
| 3 | 0.75 | R | 1.22 | 2.42 | 1.92 | 2.34 |
| 4 | 0.75 | R | 1.22 | 2.53 | 1.95 | 2.38 |
| 1 | 0.50 | R | 1.22 | 2.58 | 2.23 | 2.77 |
| 2 | 0.50 | R | 1.23 | 2.48 | 2.23 | 2.74 |
| 3 | 0.50 | R | 1.23 | 2.50 | 2.27 | 2.79 |
| 4 | 0.50 | R | 1.23 | 2.56 | 2.09 | 2.56 |
| 1 | 0.25 | R | 1.22 | 2.94 | 2.23 | 2.72 |
| 2 | 0.25 | R | 1.22 | 2.80 | 2.10 | 2.57 |
| 3 | 0.25 | R | 1.23 | 2.64 | 2.39 | 2.96 |
| 4 | 0.25 | R | 1.24 | 2.65 | 2.58 | 3.19 |

TABLE IV

(R)-CSP Results, Second Run

| Column | Concentration | Enantiomer | Selectivity | Resolution | $k'_1$ | $k'_2$ |
|---|---|---|---|---|---|---|
| 1 | 0.75 | S | 1.33 | 3.45 | 2.44 | 3.21 |
| 2 | 0.75 | S | 1.33 | 3.46 | 2.51 | 3.32 |
| 3 | 0.75 | S | 1.33 | 3.41 | 2.41 | 3.18 |
| 4 | 0.75 | S | 1.34 | 3.61 | 2.49 | 3.26 |
| 1 | 0.50 | S | 1.33 | 3.51 | 2.27 | 3.01 |
| 2 | 0.50 | S | 1.33 | 3.49 | 2.23 | 2.97 |
| 3 | 0.50 | S | 1.33 | 3.44 | 2.17 | 2.89 |
| 4 | 0.50 | S | 1.33 | 3.81 | 2.17 | 2.88 |
| 1 | 0.25 | S | 1.31 | 3.68 | 2.44 | 3.21 |
| 2 | 0.25 | S | 1.32 | 3.65 | 2.51 | 3.32 |
| 3 | 0.25 | S | 1.32 | 3.77 | 2.41 | 3.18 |
| 4 | 0.25 | S | 1.32 | 3.89 | 2.49 | 3.26 |
| 1 | 0.00 | N | 1.27 | 2.94 | 3.36 | 4.27 |
| 2 | 0.00 | N | 1.30 | 3.68 | 3.00 | 3.91 |
| 3 | 0.00 | N | 1.30 | 3.58 | 3.03 | 3.94 |
| 4 | 0.00 | N | 1.30 | 3.49 | 3.23 | 4.19 |
| 1 | 0.75 | R | 1.22 | 2.45 | 2.05 | 2.51 |
| 2 | 0.75 | R | 1.22 | 2.51 | 2.01 | 2.46 |
| 3 | 0.75 | R | 1.22 | 2.39 | 1.99 | 2.42 |
| 4 | 0.75 | R | 1.22 | 2.64 | 2.01 | 2.46 |
| 1 | 0.50 | R | 1.22 | 2.61 | 2.21 | 2.70 |
| 2 | 0.50 | R | 1.23 | 2.86 | 2.20 | 2.69 |
| 3 | 0.50 | R | 1.23 | 2.69 | 2.25 | 2.75 |
| 4 | 0.50 | R | 1.23 | 2.71 | 2.24 | 2.75 |
| 1 | 0.25 | R | 1.22 | 2.84 | 2.46 | 3.01 |
| 2 | 0.25 | R | 1.22 | 2.75 | 2.44 | 3.01 |
| 3 | 0.25 | R | 1.23 | 2.86 | 2.47 | 3.04 |
| 4 | 0.25 | R | 1.24 | 2.98 | 2.43 | 2.99 |

The combined means (both runs) for the selectivities tabulated above are as follows:

| Selectivity - No CMPA - 1.274 | | |
|---|---|---|
| Concentration | S Enantiomer | R Enantiomer |
| 0.75 | 1.334 | 1.220 |
| 0.50 | 1.330 | 1.225 |
| 0.25 | 1.313 | 1.215 |

Again the resolution is generally better when the enantiomeric CMPA of opposite chirality from the CSP is used. The mean for each run of the control is given below, with the combined means for both runs using the CMPA.

| Resolution - No CMPA, Run 1 - 2.988 No CMPA, Run 2 - 3.423 | | |
|---|---|---|
| Concentration | S Enantiomer | R Enantiomer |
| 0.75 | 3.448 | 2.489 |
| 0.50 | 3.561 | 2.624 |
| 0.25 | 3.679 | 2.808 |

TABLE V

(S)-CSP Results - First Run

| Column | Concentration | Enantiomer | Selectivity | Resolution | $k'_1$ | $k'_2$ |
|---|---|---|---|---|---|---|
| 5 | 0.75 | S | 1.21 | 2.50 | 2.97 | 3.63 |
| 5 | 0.50 | S | 1.21 | 2.58 | 2.48 | 3.63 |
| 5 | 0.25 | S | 1.22 | 3.12 | 2.97 | 3.63 |
| 5 | 0.75 | R | 1.30 | 3.63 | 2.21 | 2.87 |
| 5 | 0.50 | R | 1.29 | 3.84 | 2.39 | 3.08 |
| 5 | 0.25 | R | 1.28 | 3.82 | 2.76 | 3.54 |

TABLE VI

(S)-CSP Results - Second Run

| Column | Concentration | Enantiomer | Selectivity | Resolution | $k'_1$ | $k'_2$ |
|---|---|---|---|---|---|---|
| 5 | 0.75 | S | 1.21 | 2.51 | 2.30 | 2.79 |
| 5 | 0.50 | S | 1.22 | 2.80 | 2.75 | 3.35 |
| 5 | 0.25 | S | 1.22 | 2.97 | 2.70 | 3.29 |
| 5 | 0.75 | R | 1.30 | 3.65 | 2.20 | 2.85 |
| 5 | 0.50 | R | 1.29 | 3.72 | 2.32 | 2.99 |
| 5 | 0.25 | R | 1.29 | 3.75 | 2.74 | 3.55 |

Tables V and VI show that the improved results obtained when the chirality of the CMPA is opposite that of the CSP are consistent regardless of whether the CSP has S or R chirality. The mean values for selectivity and resolution obtained from the (S)-CSP column using CMPA's of the indicated enantiomeric form are summarized below:

| Concentration | Selectivity Enantiomer | | Resolution Enantiomer | |
|---|---|---|---|---|
| | R | S | R | S |
| 0.75 | 1.30 | 1.21 | 3.64 | 2.51 |
| 0.50 | 1.29 | 1.22 | 3.78 | 2.69 |
| 0.25 | 1.29 | 1.22 | 3.79 | 3.05 |

Again the improvement in both selectivity and resolution are readily apparent when the (R)-CMPA is used with the (S)-CSP.

EXAMPLE 6

This comparative example illustrates the close homology required for operability of the method of the present invention.

A CSP was prepared according to the following reaction:

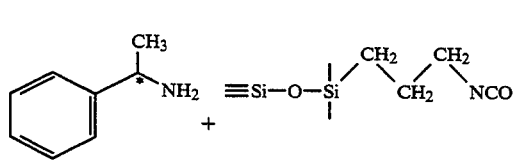

-continued

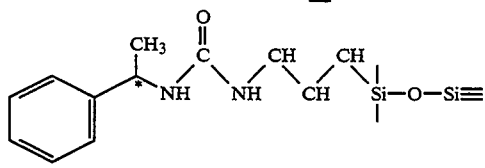

The resolution and selectivity were determined for separating (±)-N-(1-phenethyl)-3,5-dinitrobenzamide on a column containing this (R)-phenylurea CSP, using the (S)-(−)-α-methylbenzylamine and the (R)-(±)-α-methylbenzylamine,

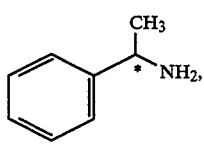

respectively, as a CMPA, and using no CMPA. Conditions used were as follows:

| | |
|---|---|
| Flow | 3 ml/minute |
| Injection Volume | 10 μl of standard (±)-N-(1-phenethyl)-3,5-dinitrobenzamide solution |
| Detection | Ultraviolet at 254 nm |
| Mobile Phase | 300:100:2 hexane:chloroform:methanol |
| CMPA Concentration | 0.25 mM (Where used) |

An average of multiple runs yielded the following results for selectivity and resolution:

| CMPA Enantiomer | Selectivity | Resolution |
|---|---|---|
| (R) | 1.25 | 2.91 |
| (S) | 1.28 | 3.52 |
| None | 1.40 | 4.08 |

A comparison of the (R) and (S) enantiomers shows once again that the CMPA of opposite chirality produces better selectivity and resolution. However, in this case the homology between the CSP and the CMPA is less in this comparative example than in the above working examples; even though the CMPA is the same α-methylbenzylamine used to produce the CSP, the CSP is a urea rather than an amine. Consequently the selectivity and resolution are better where no CMPA at all is used.

The above results clearly show that selectivity and resolution are improved over no additive when the enantiomeric CMPA having the opposite chirality to the CSP is used, so long as dose homology is maintained, and that selectivity and resolution are worse than no CMPA when the chiralities of the CMPA and CSP are the same, or when the homology is reduced.

I claim:

1. A method for separating enantiomers, diastereoisomers or mixtures thereof which comprises passing a mobile phase containing the dissolved enantiomers, diastereoisomers, or mixtures thereof, through a chromatographic column containing an enantiomeric, chiral stationary phase covalently bonded through a stable bond to a particulate support, wherein the mobile phase further contains an enantiomeric, chiral mobile-phase additive selected such that the asymmetric carbon atom or atoms of the chiral stationary phase and the groups attached thereto, excluding the linking group on the chiral stationary phase, are repeated in the chiral mobile-phase additive, but with opposite chirality, wherein the linking group on the chiral stationary phase is structurally homologous to the linking group on the chiral mobile-phase additive and wherein the enatiomertic, chiral stationary phase and the enantiomeric, chiral mobile-phase additive share the structure

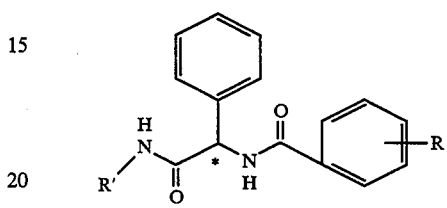

wherein R is one or two electron-withdrawing groups, and R' is a C1-C20 aryl or linear or branched alkyl group.

2. The method of claim 1 wherein the number of carbon atoms in the linking group of the chiral stationary phase is within one, more or less, of the number of carbon atoms in the linking group of the chiral mobile-phase additive.

3. The method of claim 1 wherein the number of carbon atoms in the linking group of the chiral stationary phase is the same as the number of carbon atoms in the linking group of the chiral mobile-phase additive.

4. The method of claim 1 wherein the electron-withdrawing group is nitro.

5. The method of claim 4 wherein the nitro group is a 4-nitro group.

6. The method of claim 1 wherein the electron-withdrawing group is chloro.

7. The method of claim 1 wherein the electron-withdrawing groups are 3,5-dinitro groups.

8. The method of claim 1 wherein the electron-withdrawing groups are 2,4-dinitro groups.

9. The method of claim 1 wherein the mobile phase is a solvent for the enantiomers, diastereoisomers or mixtures thereof, and for the CMPA, and is inert to the CSP, the CMPA and the enantiomers, diastereoisomers or mixtures thereof.

10. The method of claim 9 wherein the CMPA is present in the mobile phase at a concentration of at least about 0.001 millimoles per liter.

11. The method of claim 9 wherein the CMPA is present in the mobile phase at from about 0.1 millimolar to about 1 millimoles per liter.

12. The method of claim 9 wherein the CMPA is present in the mobile phase at from about 0.2 millimolar to about 0.3 millimoles per liter.

13. The method of claim 1 wherein the support is porous.

14. The method of claim 13 wherein the support is an inorganic support.

15. The method of claim 13 wherein the support is selected from the group consisting of silica and alumina.

16. The method of claim 13 wherein the support is silica.

* * * * *